US009572713B2

(12) United States Patent
Lind et al.

(10) Patent No.: US 9,572,713 B2
(45) Date of Patent: Feb. 21, 2017

(54) INTRAOCULAR PRESSURE SENSING SYSTEM FOR POSTERIOR SEGMENT DRAINAGE

(71) Applicant: NOVARTIS AG, Basel (CH)

(72) Inventors: Casey Lind, Orange, CA (US); Robert J. Sanchez, Jr., Oceanside, CA (US)

(73) Assignee: Novartis AG, Basel (CH)

( * ) Notice: Subject to any disclaimer, the term of this patent is extended or adjusted under 35 U.S.C. 154(b) by 148 days.

(21) Appl. No.: 14/481,961

(22) Filed: Sep. 10, 2014

(65) Prior Publication Data

US 2016/0067092 A1    Mar. 10, 2016

(51) Int. Cl.
*A61M 5/00* (2006.01)
*A61F 9/007* (2006.01)

(52) U.S. Cl.
CPC ... *A61F 9/00781* (2013.01); *A61M 2205/3344* (2013.01); *A61M 2210/0612* (2013.01)

(58) Field of Classification Search
CPC .................................................. A61F 9/00781
USPC ....................................................... 604/8, 9
See application file for complete search history.

(56) References Cited

U.S. PATENT DOCUMENTS

| 4,402,681 | A | * | 9/1983 | Haas | A61F 9/00781 604/175 |
| 6,050,970 | A | * | 4/2000 | Baerveldt | A61F 9/00781 604/10 |
| 7,354,416 | B2 | * | 4/2008 | Quiroz-Mercado | A61F 9/00781 604/264 |
| 8,579,848 | B2 | * | 11/2013 | Field | A61M 1/0031 604/9 |
| 2008/0228127 | A1 | * | 9/2008 | Burns | A61F 9/00781 604/9 |
| 2012/0089072 | A1 | * | 4/2012 | Cunningham, Jr. | A61F 9/00781 604/9 |
| 2013/0253402 | A1 | * | 9/2013 | Badawi | A61F 9/0017 604/8 |

* cited by examiner

*Primary Examiner* — Lesli Deak
(74) *Attorney, Agent, or Firm* — Kenneth D. Bassinger

(57) ABSTRACT

A method of implanting a treatment device into an eye of a patient comprises inserting a drainage device including a flow system, an inlet tube, and an outlet tube into a subconjunctival space. The inlet tube includes a proximal end coupled to the flow system in the subconjunctival space. The method includes passing a distal end of the inlet tube through a pars plana into a posterior segment of the eye.

23 Claims, 9 Drawing Sheets

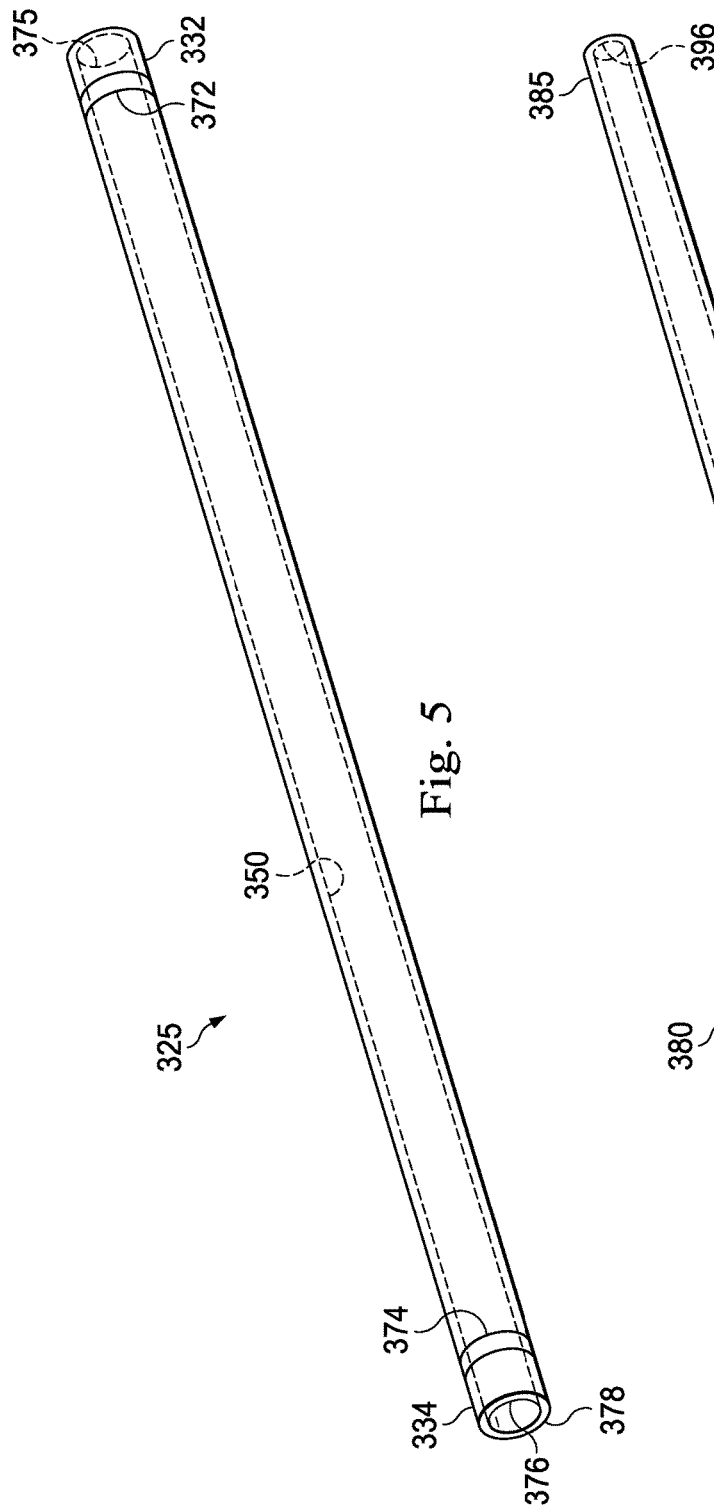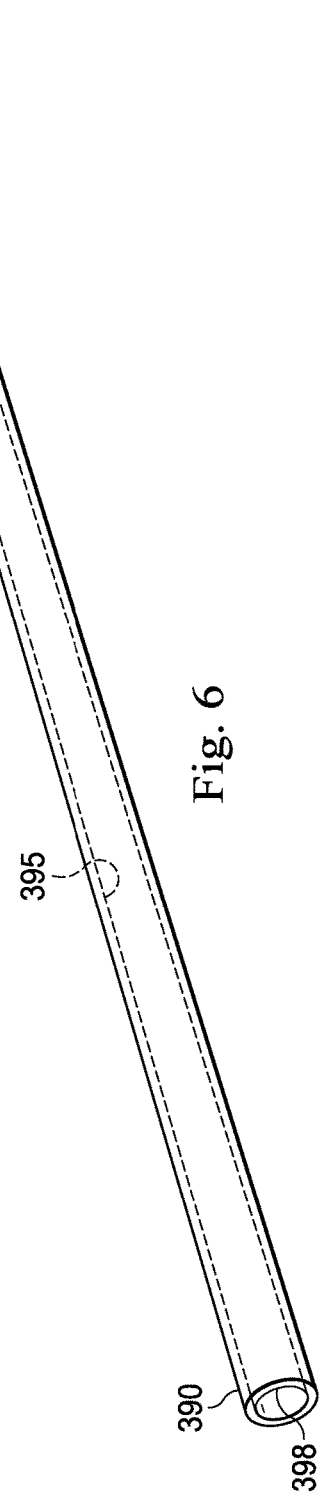

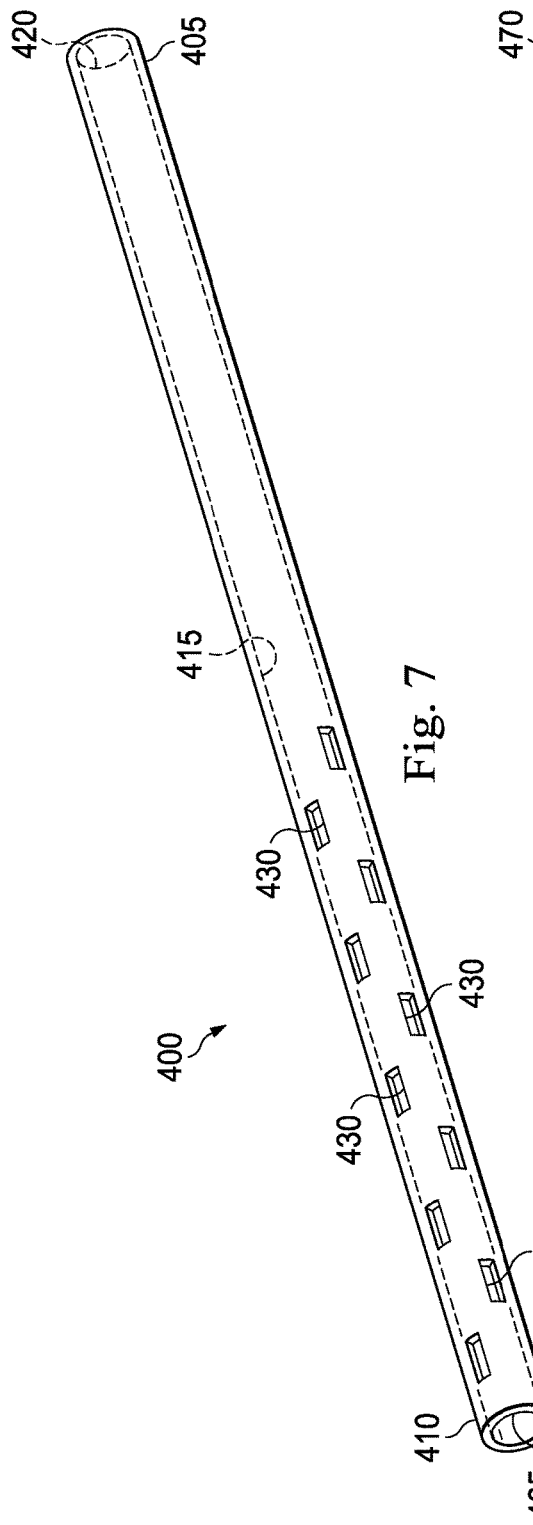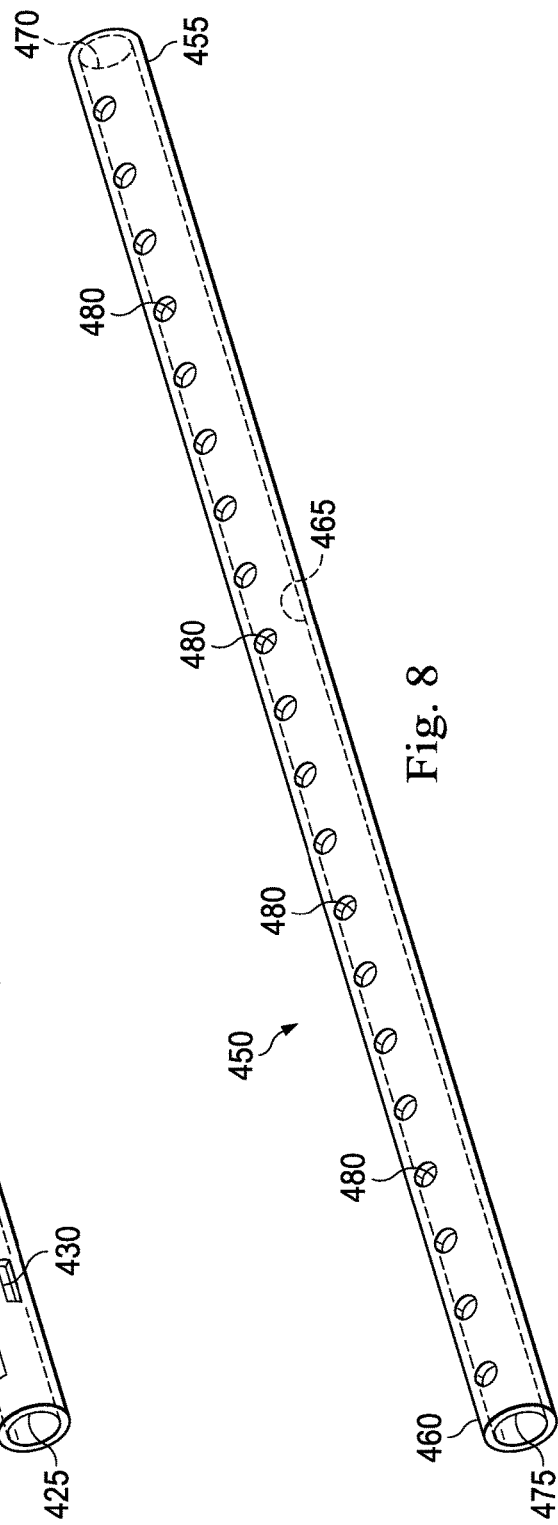

INTRAOCULAR PRESSURE SENSING SYSTEM FOR POSTERIOR SEGMENT DRAINAGE

BACKGROUND

The present disclosure relates generally to pressure/flow control systems and methods for use in treating a medical condition. In some instances, embodiments of the present disclosure are configured to be part of an IOP control system for the treatment of ophthalmic conditions.

Glaucoma, a group of eye diseases affecting the retina and optic nerve, is one of the leading causes of blindness worldwide. The tissue pressure of the intraocular contents is called the intraocular pressure (IOP). Most forms of glaucoma result when IOP increases to pressures above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision. This may be due to a direct effect of the raised pressure upon the optic nerves and/or the effect of chronic under-perfusion of the nerve head.

The eye's ciliary body continuously produces aqueous humor, the clear fluid that fills the anterior segment of the eye (the space between the cornea and lens). The aqueous humor flows out of the anterior chamber (the space between the cornea and iris) through the canalicular and the uveoscleral pathways, both of which contribute to the aqueous drainage system. The orbital globe of the eye is an essentially non-compliant sphere, allowing IOP to be influenced by a change in volume of the contents of the orbit, including both the anterior segment and the posterior segment. Thus, the delicate balance between the production and drainage of aqueous humor can influence the IOP of the eye.

FIG. 1 is a diagram of the front portion of an eye 10 that helps to explain the processes of glaucoma. In FIG. 1, representations of the lens 110, cornea 120, iris 130, ciliary body 140, trabecular meshwork 150, Schlemm's canal 160, the anterior segment 165 including both the anterior chamber 170 and the posterior chamber 175, the posterior segment 178, the sclera 180, the retina 182, the choroid 185, the limbus 190, the suspensory ligaments or zonules 195, the suprachoroidal space 200, and the conjunctiva 202 are pictured. Aqueous fluid is produced by the ciliary body 140, which lies beneath the iris 130 and adjacent to the lens 110 in the anterior chamber 170 of the anterior segment of the eye. This aqueous humor washes over the lens 110 and iris 130 and flows to the drainage system located in the angle of the anterior chamber 170. The posterior segment 178 is filled with a gel-like substance called vitreous humor. Normal regulation of IOP occurs chiefly through the regulation of the volume of aqueous humor. Similarly, however, changes in the volume of fluid (e.g., vitreous humor) within the posterior segment can affect IOP.

After production by the ciliary body 140, the aqueous humor may leave the eye by several different routes. Some goes posteriorly through the vitreous body behind the lens 110 to the retina, while most circulates in the anterior segment of the eye to nourish avascular structures such as the lens 110 and the cornea 120 before outflowing by two major routes: the conventional outflow pathway route 205 and the uveoscleral outflow route 210. The angle of the anterior chamber 170, which extends circumferentially around the eye, contains structures that allow the aqueous humor to drain. The conventional outflow pathway (or trabecular meshwork) route is the main mechanism of outflow, accounting for a large percentage of aqueous egress. The route extends from the anterior chamber angle (formed by the iris 130 and the cornea 120), through the trabecular meshwork 150, into Schlemm's canal 160. The trabecular meshwork 150, which extends circumferentially around the anterior chamber 170, is commonly implicated in glaucoma. The trabecular meshwork 150 seems to act as a filter, limiting the outflow of aqueous humor and providing a back pressure that directly relates to IOP. Schlemm's canal 160 is located just peripheral to the trabecular meshwork 150. Schlemm's canal 160 is fluidically coupled to collector channels (not shown) allowing aqueous humor to flow out of the anterior chamber 170. The arrows 205 show the flow of aqueous humor from the ciliary bodies 140, over the lens 110, over the iris 130, through the trabecular meshwork 150, and into Schlemm's canal 160 and its collector channels (to eventually reunite with the bloodstream in the episcleral vessels (not shown)).

The uveosceral route 210 accounts for the major remainder of aqueous egress in a normal eye, and also begins in the anterior chamber angle. Though the anatomy of the uveoscleral route 210 is less clear, aqueous is likely absorbed by portions of the peripheral iris 130, and the ciliary body 140, after which it passes into the suprachoroidal space 200. The suprachoroidal space 200 is a potential space of loose connective tissue between the sclera 180 and the choroid 185 that provides a pathway for uveoscleral outflow. Aqueous exits the eye along the length of the suprachoroidal space to eventually reunite with the bloodstream in the episcleral vessels.

One method of treating glaucoma includes implanting a drainage device in a patient's eye. The drainage device allows fluid to flow from the interior of the eye (e.g., from the posterior segment to a drainage site, relieving pressure in the eye and thus lowering IOP). The system and methods disclosed herein overcome one or more of the deficiencies of the prior art.

SUMMARY

In an exemplary aspect, the present disclosure is directed to a method of implanting a treatment device into an eye of a patient. In one aspect, the method includes inserting a drainage device including a flow system, an inlet tube, and an outlet tube into a subconjunctival space. In one aspect, the inlet tube includes a proximal end coupled to the flow system in the subconjunctival space. In one aspect, the method includes passing a distal end of the inlet tube into a posterior segment of the eye. In one aspect, the method includes passing a distal end of the inlet tube through a pars plana into a posterior segment of the eye.

In one aspect, passing a distal end of the inlet tube through the pars plana into the posterior segment comprises passing the inlet tube through a sclera and a choroid of the eye before the distal end enters the posterior segment.

In one aspect, the method includes using a penetrating instrument to create a passageway for the distal end of the inlet tube from the subconjunctival space through the pars plana to the posterior segment.

In another exemplary aspect, the present disclosure is directed to a treatment device for the drainage of fluid within an eye of a patient, comprising a drainage tube and a flow system. In one aspect, the drainage tube has a lumen and comprises an inlet tube portion and an outlet tube portion. In one aspect, the drainage tube is configured to convey fluid through the lumen from a posterior segment of the eye to a delivery site in the eye. In one aspect, the device includes a pressure sensor coupled to the inlet tube portion. In one aspect, the pressure sensor is configured to measure posterior segment pressure. In one aspect, the flow system is in fluid communication with the drainage tube, and is configured to control intraocular pressure by throttling flow rates of the fluid through the drainage tube in response to changes in the posterior segment pressure, which may be measured by the pressure sensor. In one aspect, the inlet tube portion is arranged to extend from the posterior segment to the flow system.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

FIGS. 5-9 illustrate perspective views of various exemplary inlet tubes according to the principles of the present disclosure.

DETAILED DESCRIPTION

Figure 1:
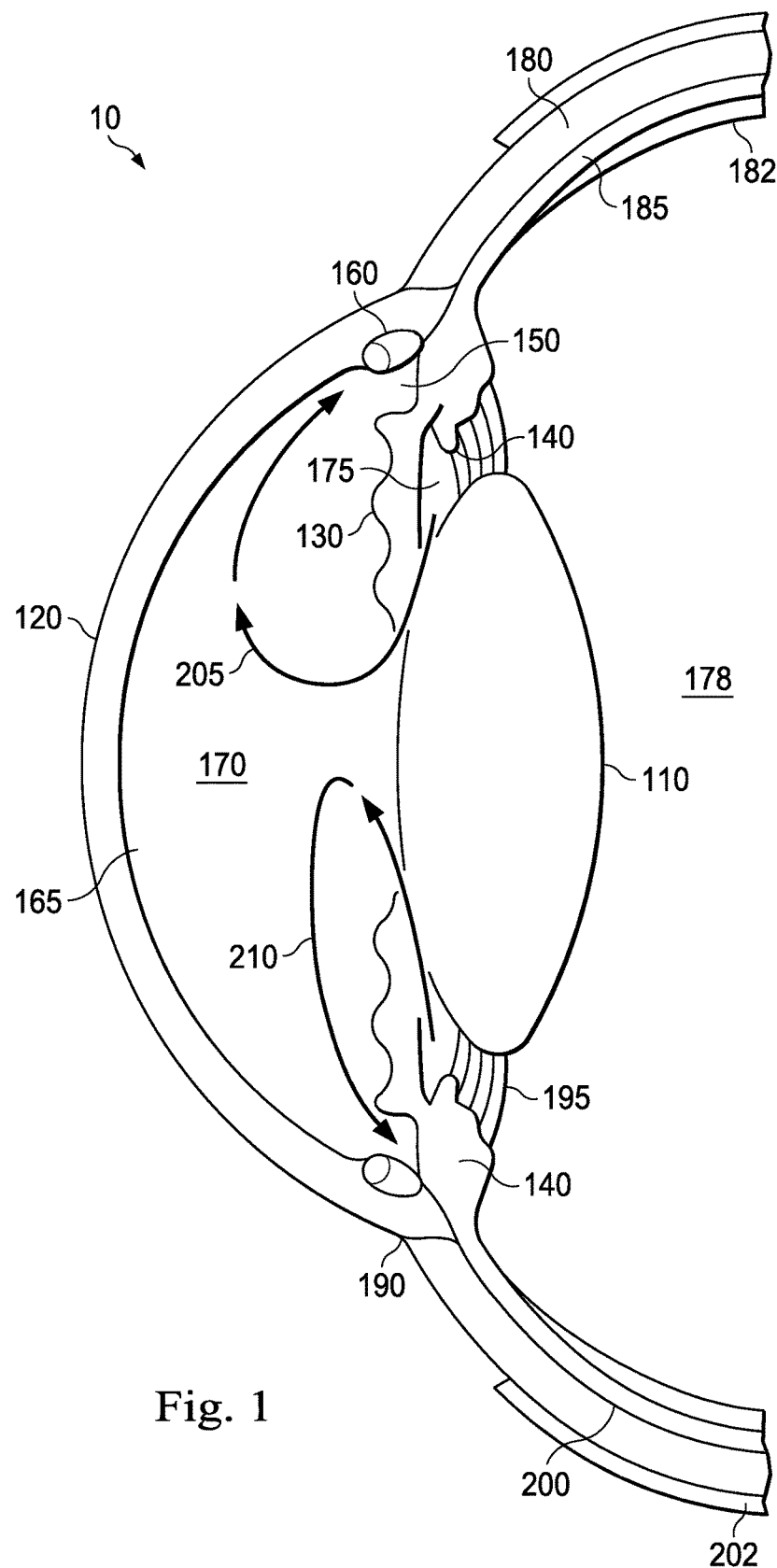
FIG. 1 is a diagram of the front portion of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The present disclosure is directed to a flow control system for treating a medical condition, such as glaucoma, by using a posterior segment pressure reference instead of an anterior chamber pressure reference. In one aspect, the system adjusts IOP by regulating fluid drainage through an implant such as a glaucoma drainage device (GDD). The system directs fluid drainage from the interior of an eye through a drainage tube to a drainage site. In one aspect, the system directs fluid drainage from the posterior segment of the eye to a drainage site through the drainage tube. In one aspect, the flow control system is implanted in the subconjuctival space, and the drainage tube extends from the posterior segment through the flow control system directly through the sclera to drain fluid into the drainage site. By enabling drainage from the posterior segment based on a posterior segment pressure reference, the surgeon can avoid entering the anterior chamber of the eye during implantation of the GDD. By not entering the anterior chamber, the risk of cataract and infection may be reduced. Thus, the devices, systems, and methods disclosed herein allow for the flow control system to reside within the subconjunctival space (or other ocular site) while providing an inlet tube to facilitate draining fluid away from the posterior segment, thereby allowing for regulation of IOP through the regulation of fluid volume within the posterior segment. In one aspect, the embodiments disclosed herein affect the operation of the GDD (e.g., a GDD allowing drainage from posterior segment of the eye) based on a posterior segment pressure reference.

Figure 2:
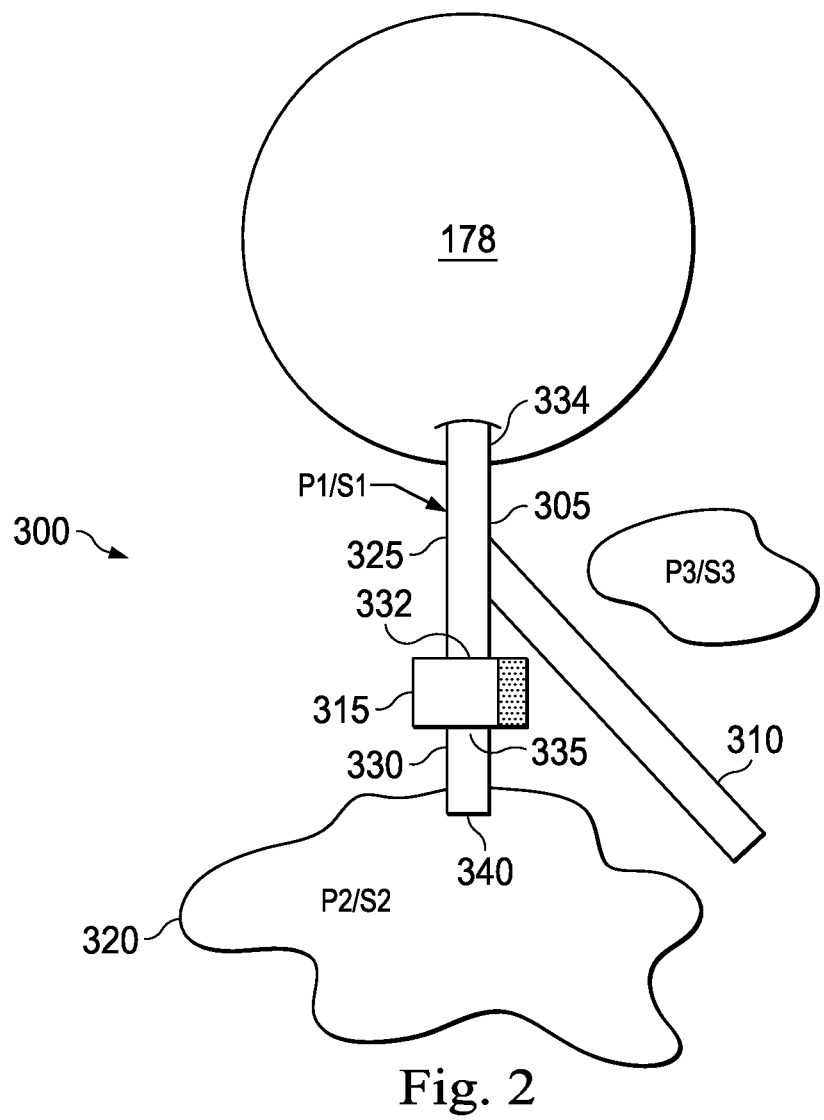
FIG. 2 is a schematic diagram of an exemplary drainage device disposed on an eye according to the principles of the present disclosure.

FIG. 2 is a schematic diagram of an exemplary drainage device or implant 300 positioned within an eye of a patient. The drainage implant 300 is designed to regulate IOP by utilizing an adjustable smart valve, passive valve, or active element (e.g., without limitation, a pump) to throttle or pump the flow of fluid out of a posterior segment 178 into the drainage site.

In this example, the implant 300 includes a drainage tube 305 and a divider 310 associated with a flow system 315. In some examples, the flow system 315 may be formed as a part of or utilized in a valve system such as those disclosed in patent application Ser. No. 13/315,329, titled "Active Drainage Systems with Pressure-Driven Valves and Electronically-Driven Pump," filed Dec. 9, 2011, which is incorporated herein by reference in its entirety.

In the embodiment pictured in FIG. 2, the implant 300 is arranged in the eye such that three areas of pressure interact with the implant: P1, P2, and P3. Pressure area P1 reflects the pressure of the posterior segment 178, pressure area P2 reflects the pressure of a drainage site 320, and pressure area P3 reflects a pressure located remotely from P1 and P2 (effectively reflecting atmospheric pressure). In some embodiments, pressure area P1 reflects the pressure located in a lumen or tube that is in fluidic communication with the posterior segment 178.

In the pictured embodiment, the drainage tube 305 drains fluid from the posterior segment 178 of the eye to the drainage location 320, which may be the suprachoroidal space 200 shown in FIG. 1. Other examples of a drainage location 320 include, but are not limited to: a subconjunctival space, a subscleral space, a supraciliary space, an episcleral vein, and other uveo-scleral pathways. The drainage tube 305 includes an inlet tube or inlet tube portion 325, which extends from the posterior segment 178 to the flow system 315, and an outlet tube or outlet tube portion 330, which extends from the flow system 315 to the drainage site 320. The inlet tube includes a proximal end 332 coupled to the flow system 315 and a distal end 334 positioned within the posterior segment 178. The outlet tube 330 includes a proximal end 335 coupled to the flow system 315 and a distal end 340 positioned within the drainage site 320.

The flow system 315 regulates IOP by throttling or inducing the flow of fluid through the tube 305, from the inlet tube 325 to the outlet tube 330. In some instances, the flow system 315 throttles the flow of fluid through the tube 305 as a function of a pressure differential. The flow system 315 may include components or elements that control pressure by regulating the amount of drainage flow through the implant 300. The flow system 315 may include any number of valves and any number of pumps, or may not include a pump or may not include a valve. In some embodiments, the flow system 315 is an active system that is responsive to signals from a processor to increase flow, decrease flow, or to maintain a steady flow as a function of pressure differentials across the valve system. In one embodiment, it does this by maintaining a valve setting at a consistent setting, or increasing or decreasing the amount that the valve is open.

In addition, the flow system 315 may incorporate pressure sensors to monitor and utilize the pressures P1, P2, and P3 to achieve a desired IOP. In some embodiments, the implant 300 responds to the pressure differentials between the pressures sensed at P1, P2, and P3 by sensors S1, S2, and S3, respectively, to control the flow system 315 and thereby throttle the flow rate of fluid through the drainage tube 305 to control IOP. In some embodiments, the various pressure differentials across the pressure areas sensed at P1, P2, and P3 (P1–P2, P1–P3, P2–P3) drive the flow system 315 and dictate the valve position or pump state to throttle the flow rate of fluid through the drainage tube 305 to control IOP. In some embodiments, the implant may include only a pressure sensor S1, and may be coupled with a separate drainage device that includes the remaining sensors S2 and S3. Such an implant may lack a drainage tube 305 and/or a flow system 315.

In the embodiment shown, a pressure sensor S1 measures the pressure in the tube 305 upstream from the flow system 315 and downstream from the posterior segment 178. In this manner, the pressure sensor S1 measures the pressure in the posterior segment 178. The expected measurement discrepancy between the true posterior segment pressure and that measured by S1 when located in a tube downstream of the posterior segment (even when located between the sclera and the conjunctiva) is negligible.

A pressure sensor S2 is located at the drainage site 320 or in fluid communication with the drainage site 320 via the outlet tube 320. As such, the pressure sensor S2 may be located in the subconjunctival space, suprachoroidal space 200, a subscleral space, a supraciliary space, an episcleral vein, or another uveo-scleral pathway, for example.

In some embodiments, the divider 310 acts as a barrier that separates the pressure region measured by the pressure sensor S3 from the pressure region measured by the pressure sensor S2. In some embodiments, the system includes other barriers that separate the sensors S1, S2, and S3. These barriers may be elements of the flow system 315 itself. In FIG. 2, the pressure region measured by the pressure sensor S3 is physically separated from the pressure region measured by the pressure sensor S2 by the divider 310. The divider 310 is a physical structure that separates the drainage area 306 from the isolated location of pressure region measured by the pressure sensor S3. The divider 310 may be sutured and/or healed tissue.

Generally, IOP is a gauge pressure reading—the difference between the absolute pressure in the eye (as measured by sensor S1) and atmospheric pressure (as measured by sensor S3). Atmospheric pressure, typically about 760 mm Hg, often varies in magnitude by 10 mmHg or more depending on weather conditions or indoor climate control systems. In addition, the effective atmospheric pressure can vary significantly—in excess of 300 mmHg—if a patient goes swimming, hiking, riding in an airplane, etc. Such a variation in atmospheric pressure is significant since IOP is typically in the range of about 15 mm Hg. Thus, for accurate monitoring of IOP, it is desirable to have pressure readings for the interior chamber of the eye (as measured by sensor S1) and atmospheric pressure in the vicinity of the eye (as measured by sensor S3).

In one embodiment of the present invention, pressure readings are taken by the pressure sensors S1 and S3 simultaneously or nearly simultaneously over time so that the actual IOP can be calculated (as S1–S3 or S1–f(S3), where f(S3) indicates a function of S3). In another embodiment of the present invention, pressure readings taken by the pressure sensors S1, S2, and S3 can be used to control a device that drains aqueous from the posterior segment 178. For example, in some instances, the implant 300 reacts to the pressure differential across S1 and S3 continuously or nearly continuously so that the actual IOP (as S1–S3 or S1–f(S3)) can be responded to accordingly.

Figure 3:
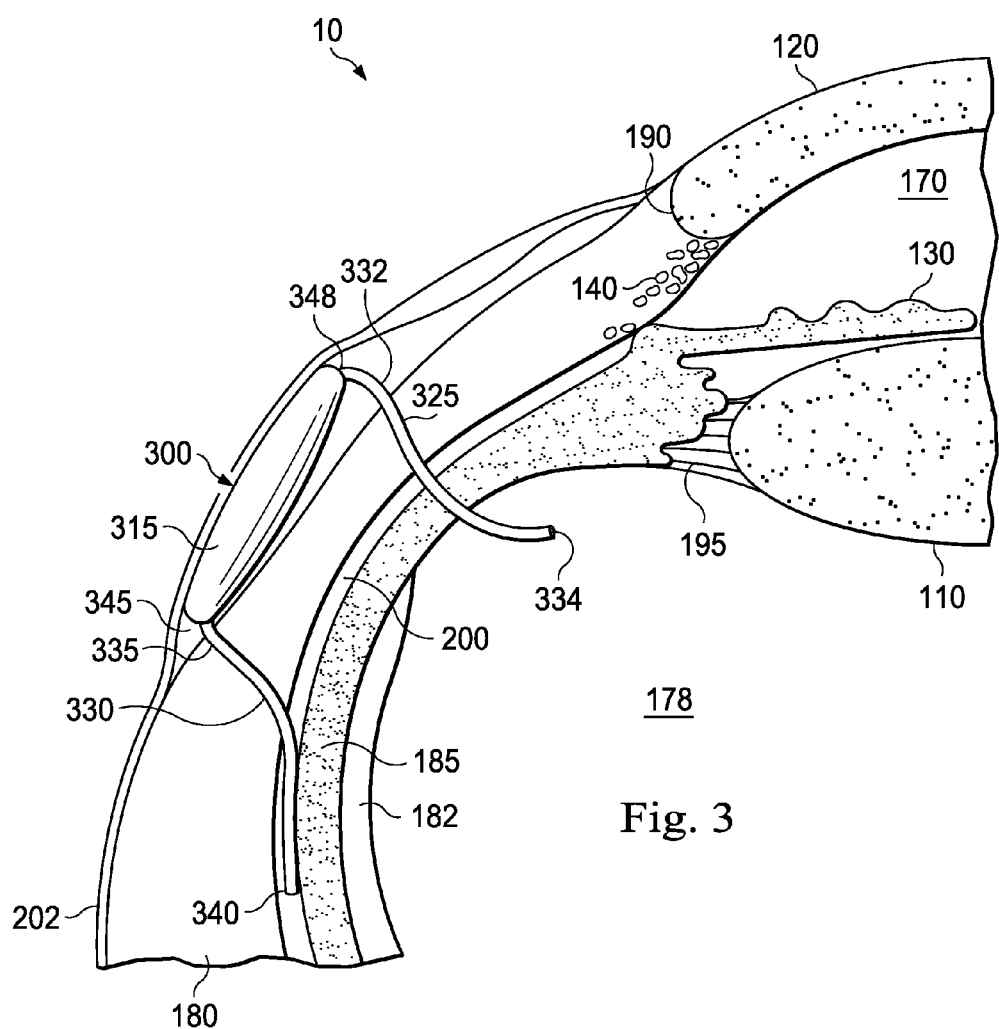
FIG. 3 illustrates a cross-sectional side view of an exemplary drainage device positioned within an eye according to one embodiment of the present disclosure.

FIG. 3 illustrates a cross-sectional side view of the drainage implant 300 positioned within the eye 10 according to one embodiment of the present disclosure. In the pictured embodiment, the drainage implant 300 is shaped and configured to be implanted within the subconjunctival space, between the conjunctiva 202 and the sclera 180. In some embodiments, the bulk of the implant 300 may be positioned within the eye in a subconjunctival space 345 between the conjunctiva 202 and the sclera 180 with an anterior border 348 of the flow system 315 positioned such that the implant does not come into contact with the optic nerve. For example, in one embodiment, depending upon the size and shape of the implant, the implant 300 may be positioned with the anterior border approximately 8 to 10 mm posterior to the limbus 190 (the border between the cornea and the sclera). The drainage implant 300 may be held in place within the eye via anchoring sutures, the angle of implantation and surrounding anatomy, or by a spring force or other mechanisms that stabilize the implant 300 relative to the patient's eye. The inlet tube 325 and the outlet tube 330 are coupled to the flow system 315 at the location of the subconjunctival space 345, and extend from the subconjunctival space 345 into the posterior segment 178 and the delivery site, respectively, as discussed below. In the pictured embodiment, the outlet tube 330 is positioned with the distal end 340 positioned within the suprachoroidal space 200.

Figure 4:
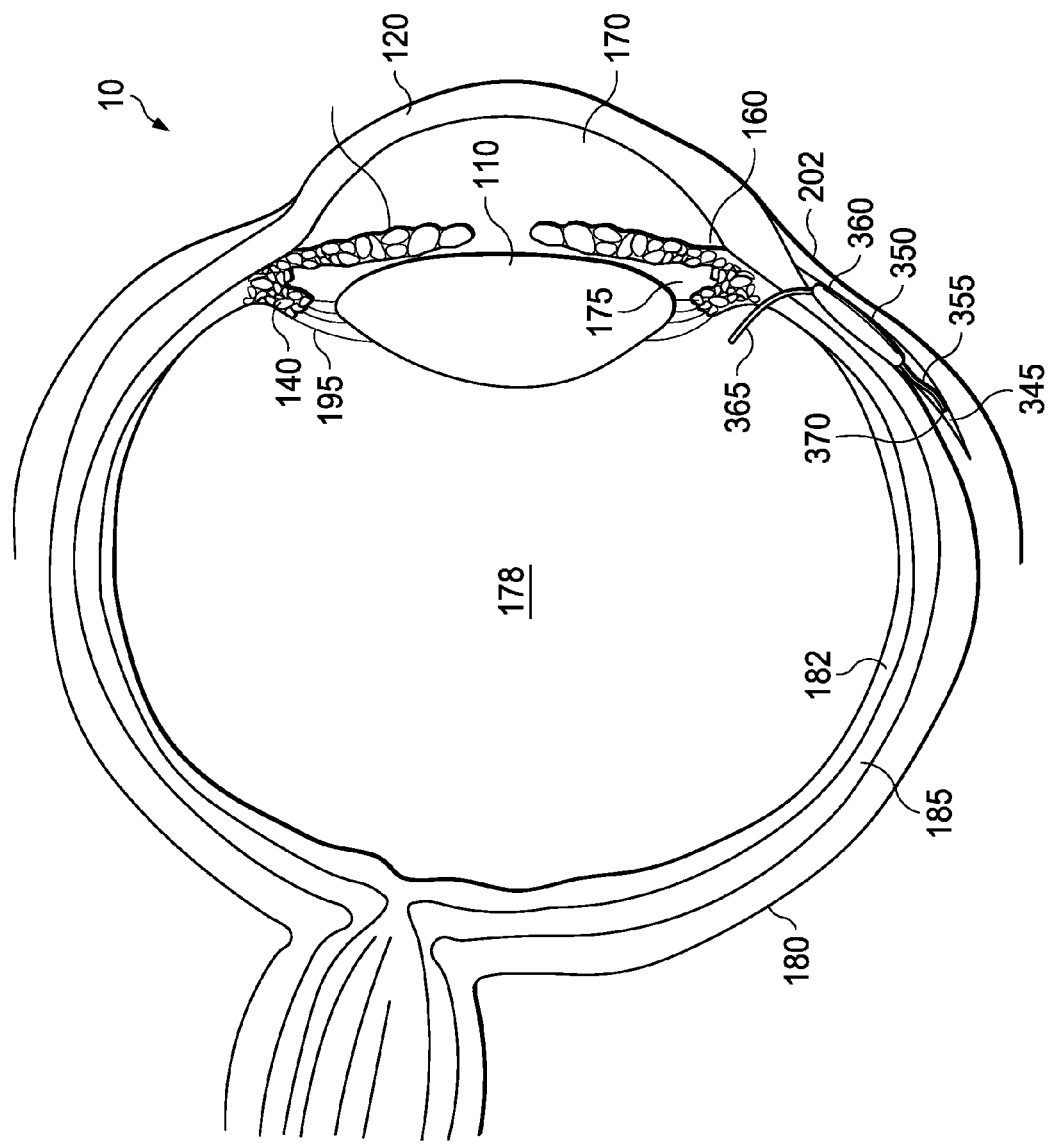
FIG. 4 illustrates a cross-sectional side view of an exemplary drainage implant positioned within an eye according to one embodiment of the present disclosure.

FIG. 4 illustrates a cross-sectional side view of the drainage implant 350 positioned within the eye 10 according to another embodiment of the present disclosure. In the pictured embodiment, the drainage implant 350 is shaped and configured to be implanted within the subconjunctival space, between the conjunctiva 202 and the sclera 180. The drainage implant 350 is substantially similar to the drainage implant 300 except for the differences noted herein. For example, the drainage device 350 includes an outlet tube 355 that is shaped and configured to extend from a flow system 360 into the subconjunctival space 345, instead of the suprachoroidal space 200. Thus, in the pictured embodiment, the delivery site is the subconjunctival space (and/or a bleb). The drainage implant 350 may be held in place within the eye via anchoring sutures, the angle of implantation and surrounding anatomy, or by a spring force or other mechanisms that stabilize the implant 350 relative to the patient's eye. An inlet tube 365 and the outlet tube 355 are coupled to the flow system 360 at the location of the subconjunctival space 345. The inlet tube 360 extends from the subconjuctival space 345 into the posterior segment 178. In the pictured embodiment, the outlet tube 355 is positioned with a distal end 370 of the outlet tube positioned within the subconctival space 345.

FIG. 5 illustrates the exemplary inlet tube 325 shown in FIGS. 2 and 3. The inlet tube 325 is shaped and configured as an elongate, flexible, hollow cylinder including the proximal end 332, the distal end 334, and a lumen 350 extending from the proximal end 332 to the distal end 334. In the pictured embodiment, the inlet tube 325 includes a proximal marker 372 and a distal marker 374. In other embodiments, the inlet tube may be of any of a variety of different shapes with or without markers. The proximal end 332 is coupled to the flow system 315 (as shown in FIG. 2), and is configured to deliver fluid into the flow system 315. The distal end 334 is configured to allow the ingress of fluid (e.g., aqueous humor) from the posterior segment 178 into the lumen 350. The lumen 350 serves as a passageway for the flow of fluid through the inlet tube 325 from the posterior segment 178 into the flow system 315. In the pictured embodiment, the lumen 350 has a uniform luminal diameter along the length of the tube 330. In other embodiments, the luminal diameter can vary in diameter along the length of the tube. For example, in some embodiments, the luminal diameter may taper along the length of the tube so as to achieve a desired flow rate through the tube.

The inlet tube 325 includes a single proximal aperture 375 at the proximal end 332 for ingress of fluid, and a single distal aperture 376 for egress of fluid. Both apertures 375, 376 are in communication with the lumen 350. However, other embodiments may include any number and arrangement of apertures that communicate with the lumen 350, as discussed below. In one embodiment, fluid can flow from the flow system 315 into the proximal aperture 375 at the proximal end 332 of the inlet tube 325, through the lumen 350, and out the distal aperture 376 at the distal end 334 into the delivery site.

In the pictured embodiment, the inlet tube 325 has an atraumatic distal end 334, shaped and configured with blunt edges 378 to prevent inadvertent injury to ocular tissues during implantation or if the tube 325 moves after implantation. In some embodiments, the edges 378 may be shaped in an atraumatic manner, such as by having a rounded profile. In some embodiments, the edges 378 may be manufactured of or be coated with a soft material. In other embodiments, the distal end 334 may be shaped and configured to permit the inlet tube 325 to pierce ocular tissue and enter the posterior segment 178 without the assistance of a delivery device or a pre-created pathway from the exterior of the eye 10 into the posterior segment 178. For example, in some embodiments, the edges 378 may be beveled or otherwise shaped to be sufficiently sharp to cut through ocular tissues.

In some embodiments, the distal end 334 has a column strength sufficient to permit the inlet tube 325 to be inserted into the posterior segment 178 such that the distal aperture 376 tunnels through the ocular tissue without structural collapse or degradation of the tube 325. In some embodiments, the column strength is sufficient to permit the tube 325 to tunnel through ocular tissues into the posterior segment 178 without any structural support from an additional structural such as a delivery device. In other embodiments, a delivery device may be used to facilitate the progress of the inlet tube 325 through the ocular tissue toward the posterior segment 178.

The inlet tube 325 may include one or more features that aid in properly positioning the tube in the eye 10. For example, the markers 372, 374 comprise positional indicators that can be used to accurately position the tube 325 in the eye. The marker 372 is positioned adjacent the proximal end 332 of the tube 325, and the marker 374 is positioned adjacent the distal end 334 of the tube 325. In other embodiments, the tube 325 may include any number and arrangement of markers. The markers 342, 344 may comprise visual, tomographic, echogenic, or radiopaque markers. In one exemplary method of using the markers to properly position the inlet tube 325, the distal end 334 of the inlet tube 325 may be inserted into the posterior segment 178 until either the marker 374 or the marker 372 is aligned with an appropriate anatomic structure or surgical indicator (e.g., an anatomic landmark within the posterior segment 178 such as a posterior margin of the ciliary body 140 or a suture within the sclera, respectively). For example, the surgeon may advance the distal end 334 into the posterior segment 178 until the marker 372 aligns with an appropriate anatomic structure, such as, by way of non-limiting example, the scleral spur, the limbus, or the trabecular meshwork, thereby indicating that an adequate length of the tube 325 has entered the posterior segment 178.

In the pictured embodiment, the inlet tube 325 has a substantially uniform diameter along its entire length. In exemplary embodiments, the outer diameter of the inlet tube may range in size from about 0.010 in (0.254 mm) to 0.040 in (1.016 mm). In one embodiment, the outer diameter of the inlet tube 325 may be 0.025 in (0.635 mm). However, this disclosure supports inlet tubes of different shapes and dimensions, and inlet tubes of the present disclosure may be of any shape and any dimension that may be accommodated by the eye.

Although the inlet tube 325 is shown having a circular cross-sectional shape, the inlet tube may have any of a variety of cross-sectional shapes, including without limitation, an ovoid, elliptical, square, rhomboid, or rectangular shape. In some embodiments, the inlet tube may vary in cross-sectional shape along its length. The particular cross-sectional shape may be selected to facilitate easy insertion into the eye, and may be dependent upon the method of insertion planned. In some embodiments, the inlet tube 325 may have a predetermined radius of curvature that conforms to a particular path of curvature from site of implantation of the flow system 315 to the posterior segment 178 (e.g., from the subconjunctival space 345 to the posterior segment 178). In other embodiments, the inlet tube 325 may be sufficiently flexible to assume the radius of curvature between the implantation location to the posterior segment 178 after implantation.

As mentioned above, the pictured inlet tube 325 has a substantially uniform diameter along its entire length. In other embodiments, as shown in FIG. 6, the diameter of the inlet tube may vary along its length. FIG. 6 illustrates an exemplary inlet tube 380 including a proximal end 385 and a distal end 390 with a lumen 395 extending therebetween. The tube 380 is substantially similar to the inlet tube 325 except for the differences described herein. The inlet tube 380 includes a proximal aperture 396 and a distal aperture 398. The diameter of the inlet tube 380, and consequently the diameter of the lumen 395, tapers from the distal end 390 to the proximal end 385. The diameter increases from the proximal aperture 396 to the distal aperture 398. Other embodiments may have other configurations of varying diameter. The taper may exist along the entire length of the tube or may exist along only one or more portions of the tube (e.g., the distal portion). For example, in other embodiments, the inlet tube may taper from a proximal end to a distal end (e.g., introducing a pressure gradient that may help clogged particles to progress toward the flow system 315 at the proximal end 385 of the tube 380), or widen one in a middle portion of the tube. In exemplary embodiments, the inner diameter of the inlet tube 380 (i.e., the diameter of the lumen 395) may range in size from about 0.005 in (0.127 mm) to 0.100 in (2.54 mm). In particular, the inner diameter of the inlet tube 380 may range in size from about 0.005 in (0.127 mm) to 0.050 in (1.27 mm) at the proximal aperture 396, and may range in size from about 0.020 in (0.508 mm) to 0.100 in (2.54 mm) at the distal aperture 398. In one example, the inner diameter of the inlet tube 380 may be 0.025 in (0.635 mm) at the proximal aperture 396, and may be 0.035 in (0.889 mm) at the distal aperture 398.

In the embodiment shown in FIG. 5, as mentioned above, the inlet tube 325 includes the single proximal aperture 375 at the proximal end 332 for egress of fluid into the flow system 315, and a single distal aperture 376 for ingress of fluid. In other embodiments, as indicated in FIGS. 7 and 8, the inlet tube can include a plurality of apertures through which fluid may enter the tube. FIG. 7 illustrates an inlet tube 400 according to one embodiment of the present disclosure. The tube 400 is substantially similar to the inlet tube 325 except for the differences described herein. The tube 400 includes a proximal end 405, a distal end 410, and a lumen 415 extending from the proximal end 405 to the distal end 410. In addition to a proximal aperture 420 and a distal aperture 425, both of which are in communication with the lumen 415, the inlet tube 400 includes a plurality of holes 430 located along at the length of the inlet tube 400. The holes 430 are in fluid communication with the lumen 415, and allow fluid to enter the lumen 415 of the inlet tube 400 from the posterior segment 178.

In the pictured embodiment, the holes 430 are interspersed in a staggered pattern along the distal portion of the tube 400, but, in other embodiments, the holes may be arranged in any of a variety of patterns, both asymmetrical and symmetrical, along any portion (or entirety) of the tube. In FIG. 7, the illustrated holes 400 are shaped as rectangular apertures, but, in other embodiments, the holes may have any of a variety of shapes, including, without limitation, circular, ovoid, rhomboid, and square. It should be noted that the spatial configuration, size, and angle of the holes may vary in different embodiments. Multiple apertures or holes in the tube guard against the blockage of flow through the tube in instances where other holes or apertures may be blocked. In some embodiments, the holes may function as visual markers to aid in positioning the inlet tube 400 within the eye.

For example, FIG. 8 illustrates an inlet tube 450 according to another embodiment of the present disclosure. The tube 450 is substantially similar to the inlet tube 400 except for the differences described herein. The tube 450 includes a proximal end 455, a distal end 460, and a lumen 465 extending from the proximal end 455 to the distal end 460. In addition to a proximal aperture 470 and a distal aperture 475, both of which are in communication with the lumen 465, the inlet tube 450 includes a plurality of holes 480 located along at the entire length of the inlet tube 450. The holes 480 are in fluid communication with the lumen 465, and allow fluid to enter the lumen 465 of the inlet tube 450 from the space surrounding the tube 450 (e.g., within the posterior segment 178). In FIG. 8, the illustrated holes 480 are spaced symmetrically along the entire length of the tube 450, and the holes 480 have a circular shape.

Figure 9:
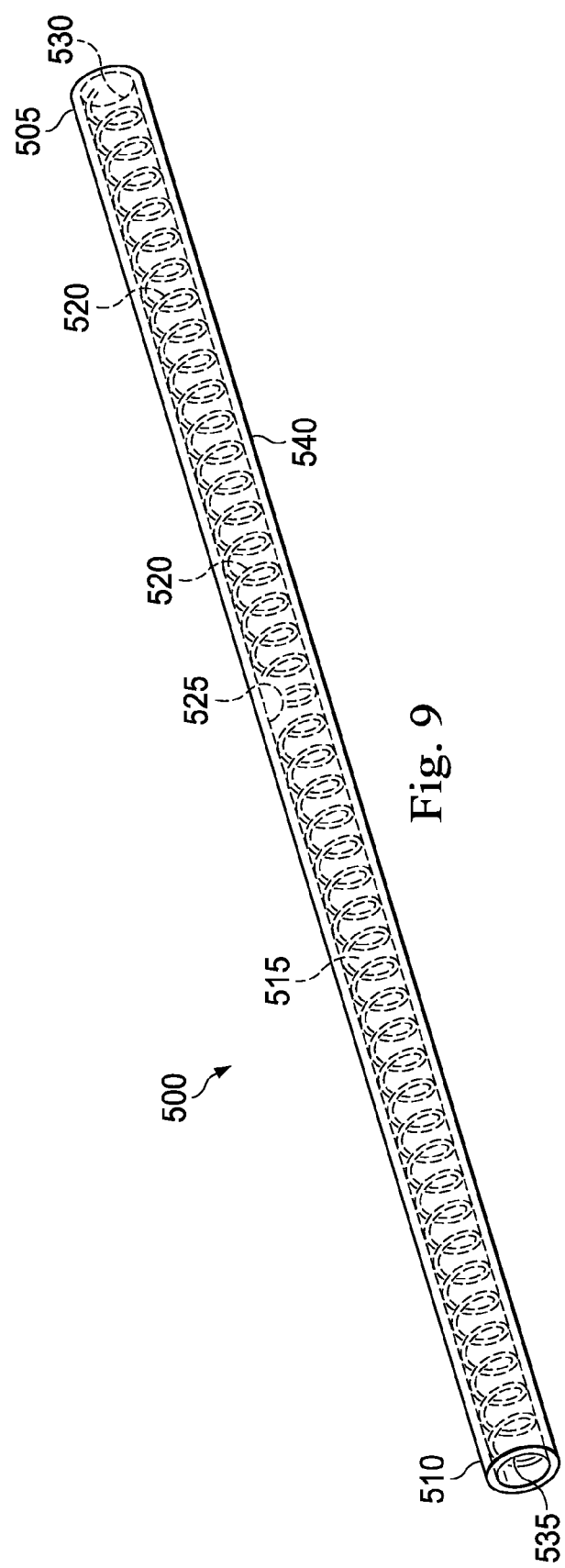

FIG. 9 illustrates an inlet tube 500 according to another embodiment of the present disclosure. The tube 500 is substantially similar to the inlet tube 325 except for the differences described herein. The tube 500 includes a proximal end 505, a distal end 510, and a lumen 515 extending from the proximal end 505 to the distal end 510. The inlet tube 500 includes a plurality of drainage features 520 located along an interior or luminal wall 525 of the tube 500. In the pictured embodiment, the drainage features 520 comprise rungs of a spiral shape extending between a proximal aperture 530 and a distal aperture 535. The drainage features 520 are shaped and arranged within the tube to facilitate the passage of fluid through the tube from the distal aperture 535 to the proximal aperture 530 and toward the flow system 315.

In FIG. 9 the illustrated spiral drainage features 520 are spaced symmetrically along the entire length of the tube 500. In other embodiments, the drainage features may be arranged symmetrically or asymmetrically, and may be arrayed along only a portion of the tube. In other embodiments, the drainage features 520 may comprise any of a variety of shapes, including, without limitation, protrusions such as nubs or ribs, indentations, dimples, columns, or helices.

An inlet tube described herein may be flexible along its entire length, may have a predetermined stiffness along its entire length, or may have a varying degree of stiffness or flexibility along its entire length. Thus, the inlet tubes may be made from any of a variety of flexible, rigid, or composite materials. In particular, the inlet tubes described herein may be made from any of a variety of biocompatible materials having the requisite flexibility and hoop strength for adequate lumen support and drainage through the lumen after implantation. Such materials include, without limitation, silicone tubing, reinforced silicone tubing, PEEK, polycarbonate, or other flexible materials. In some instances, the tube may be scored or otherwise imprinted for added flexibility throughout the tube or only in one or more portions of the tube.

Any of the embodiments of the inner tube described herein may be coated on its inner luminal surface (e.g., the luminal wall 525 shown in FIG. 9) with one or more drugs or other materials designed to help maintain the patency of the lumen. Likewise, any of the embodiments of the inlet tube described herein may be coated on its outer surface (e.g., an outer surface 540 shown in FIG. 9) with one or more drugs or other materials designed to discourage immune response or ocular tissue growth around the inlet tube to decrease the likelihood of implant rejection or clogging of the distal aperture (e.g., within the posterior segment 178). Such drugs or other materials may be contained within a polymeric coating applied to the tube.

Figure 10:
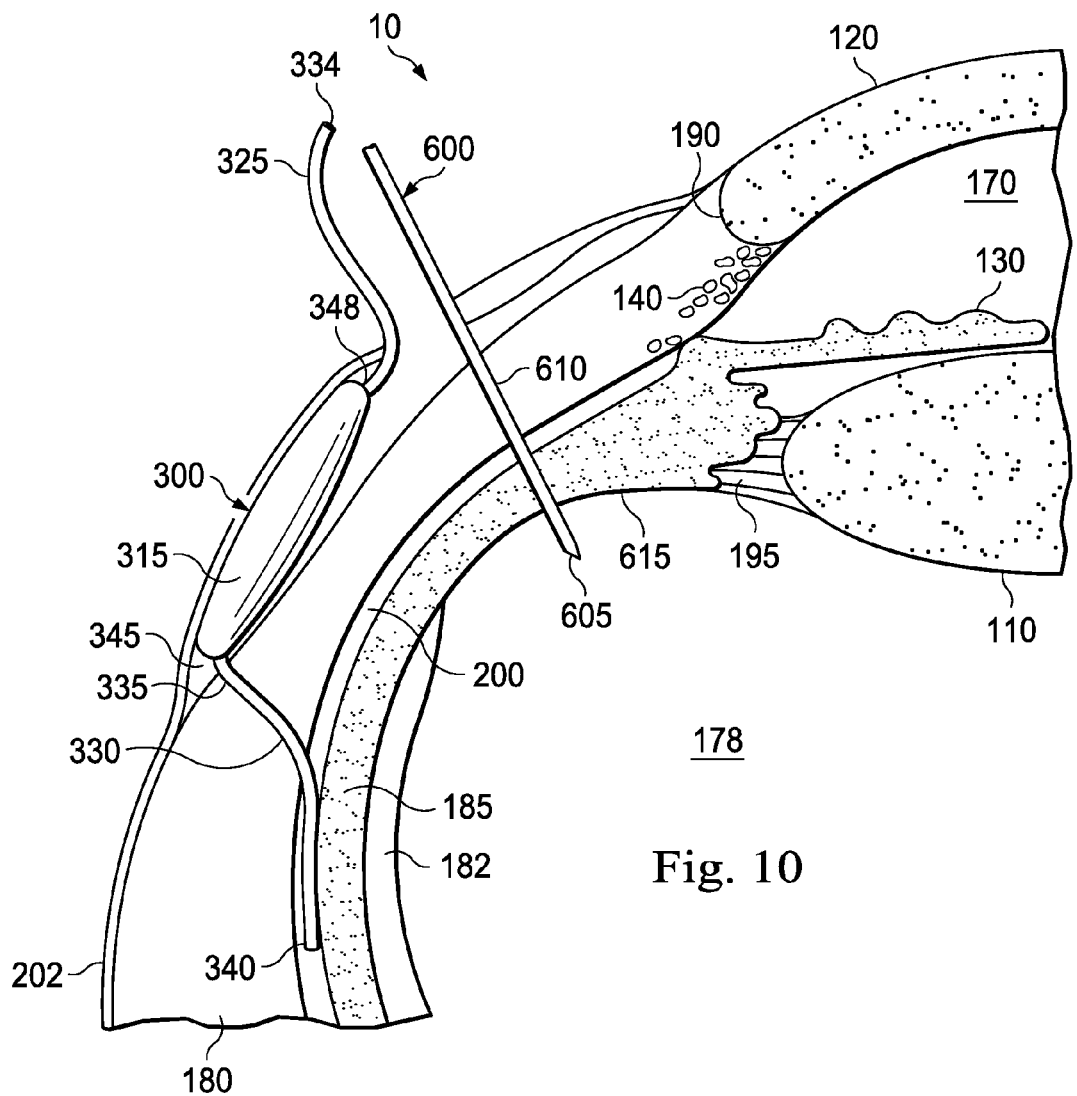
FIG. 10 illustrates a cross-sectional side view of an exemplary drainage implant and an exemplary penetrating device positioned within an eye according to one embodiment of the present disclosure.
Figure 11:
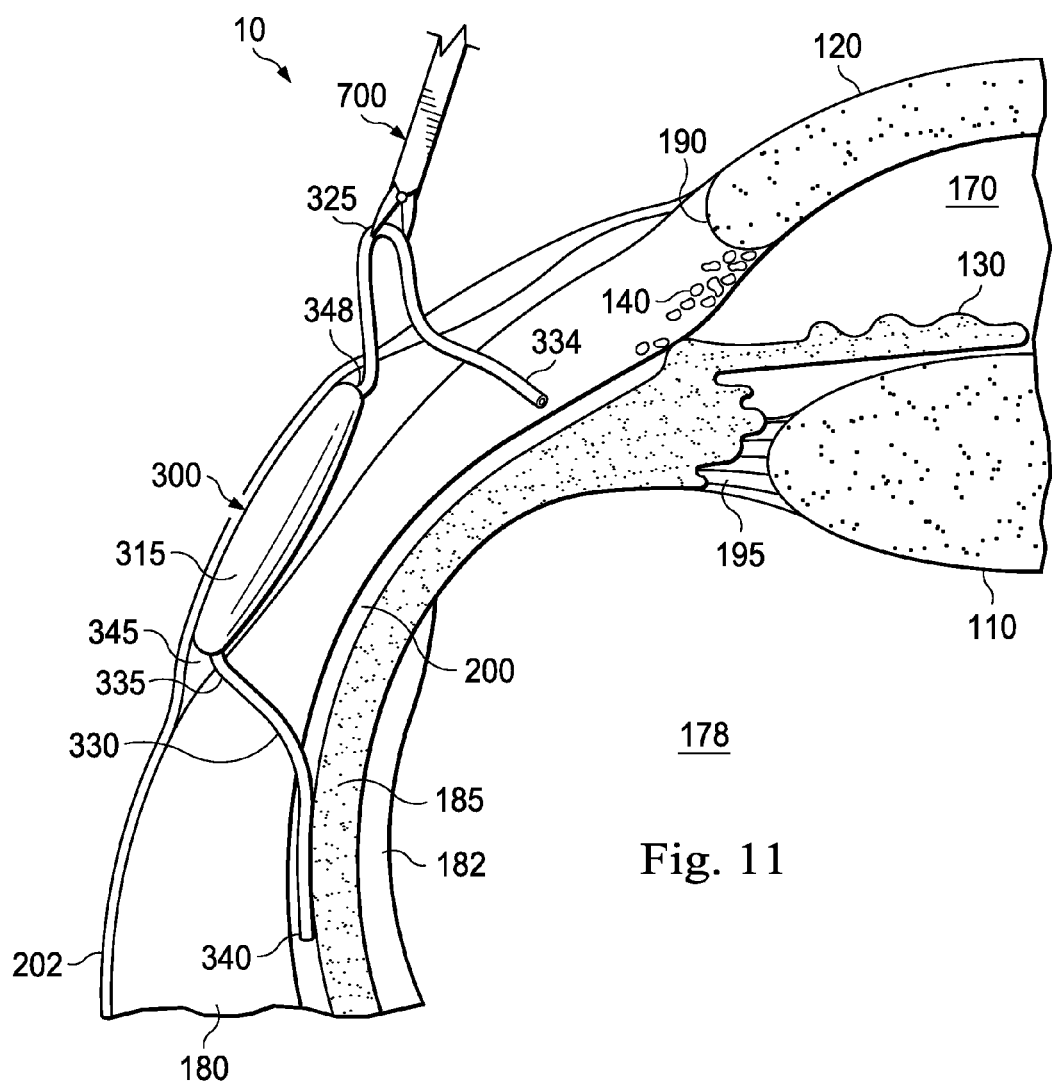
FIG. 11 illustrates a cross-sectional side view of an exemplary drainage implant positioned within an eye and an exemplary delivery device according to one embodiment of the present disclosure.

FIGS. 3, 10, and 11 illustrate exemplary methods of implanting the drainage implant 300 in the eye 10. As described above, the implant 300 includes the inlet tube 325, the flow system or body 315, and the inlet tube 325. As shown in FIG. 3, the body or flow system 315 of the implant 300 is positioned within the eye in the subconjunctival space 345 between the conjunctiva 202 and the sclera 180. The inlet tube 325 allows fluid to flow from the posterior segment 178 to the flow system 315 positioned within the subconjunctival space 345. The inlet tube 325 and the outlet tube 330 are coupled to the flow system 315 at the location of the subconjunctival space 345. In the pictured embodiment, the inlet tube 325 extends from the posterior segment 178 (from a position posterior to the ciliary body 140), through the choroid 185, through the subconjunctival space 345, through the sclera 180, and into the subconjunctival space 345 where it joins the flow system 315. The inlet tube 325 allows fluid (e.g., vitreous humor) to exit the posterior segment 178 and flow toward the flow system 315. In the pictured embodiment, the outlet tube 330 extends from the flow system 315 in the subconjunctival space 345 through the sclera 180 before entering the suprachoroidal space 200. The outlet tube 330 allows fluid to drain from the flow system 315 into the suprachoroidal space 200. In other embodiments, as illustrated by FIG. 4, the outlet tube 330 may extend to a different delivery site, such as the subconjunctival space 345.

As shown in FIGS. 10 and 11, a surgeon may insert the outlet tube 330 and the flow system 315 of the drainage implant 300 into the subconjunctival space 345 before inserting the inlet tube 325 into the posterior segment 178. In other embodiments, the surgeon may insert the inlet tube 325 into the posterior segment before inserting the remainder of the drainage implant 300 into the eye 10. In one embodiment, the surgeon may use one or more surgical instruments to create a pathway for the inlet tube (and/or the remainder of the implant 300) prior to (or during) implantation of the drainage implant 300. In particular, the surgeon may employ this technique when the inlet tube 325 includes a blunt or rounded atraumatic distal end (e.g., the distal edges 378 in FIG. 5). FIG. 10 illustrates a tunneling or penetrating instrument 600 being inserted through the conjunctiva 202, through the subconjunctival space 345, through the sclera 180, and into the posterior segment 178. The penetrating instrument 600 includes a sharp distal end 605 suitable for puncturing and tunneling through ocular tissue. In some embodiments, the penetrating instrument 600 may be steerable, articulating, or shapeable in a manner that facilitates the proper approach of the instrument 600 toward the desired ocular tissues.

While the penetrating instrument 600 is being employed to create a tunnel through the eye 10, the inlet tube 325 may remain outside the eye 10, as shown, or may be positioned within the subconjunctival space 345. After removing the penetrating instrument 600 from the eye, the surgeon may guide the distal end 334 of the inlet tube 325 through a tunnel 610 created by the penetrating instrument 600 (which may exist as a potential space when the penetrating instrument 600 is removed) toward the posterior segment 178. In the pictured embodiment, the tunnel 610 extends through a pars plana 615 of the eye 10 (thereby avoiding injury to the retina 182). The surgeon may use a delivery instrument (not shown) to grasp the inlet tube 325 and direct the distal end 334 through the tunnel 610 until the distal end enters the posterior segment 178. In some instances, the surgeon may observe the location of positional markers (e.g., the proximal and/or distal markers 372, 374 shown in FIG. 5) relative to the eye 10 to judge whether inlet tube 325 has been correctly positioned.

In other instances, as shown in FIG. 11, the inlet tube 325 may include a sufficiently strong or sharp distal end 334 to tunnel through the sclera 180 and the choroid 185 without the aid of another penetrating instrument. In the pictured embodiment, the distal end 334 is sufficiently sharp to penetrate the conjunctiva 202, the sclera 180, and the choroid 185 to enter the posterior segment 178. In such cases, the surgeon may grasp the inlet tube 325 with a delivery instrument 700 (e.g., forceps) to guide the direction of the distal end 334 through the ocular tissues toward the posterior segment 178. Upon completed delivery of the inlet tube 325 into the posterior segment 178, as shown in FIG. 3, the inlet tube 325 extends from the flow system 315 in the subconjunctival space 345, through the sclera 180 (and, in the pictured embodiment, through the suprachoroidal space 200), and into the posterior segment 178 where the distal end 334 is surrounded by fluid (e.g., vitreous humor) within the posterior segment 178. In some instances, the surgeon may observe the location of positional markers (e.g., the proximal and/or distal markers 372, 374 shown in FIG. 5) relative to the eye 10 to judge whether an adequate length of the inlet tube 325 has been positioned within the posterior segment 178 to enable effective drainage.

Embodiments in accordance with the present disclosure provide a fluid drainage device which utilizes an adjustable smart valve, a passive valve, or a pump to drain fluid from the posterior segment to a drainage site (e.g., the subconjunctiva, the suprachoroidal space, and other ocular sites). In particular, embodiments in accordance with the present disclosure provide a fluid drainage device which utilizes an adjustable smart valve, a passive valve, or a pump to drain fluid from the posterior segment to flow system via an inlet tube extending into the posterior segment. The posterior segment pressure sensors described herein may be coupled with a separate drainage device or drainage tube to measure and log IOP, or to control an active GDD where IOP measurements are needed for closed loop control of drainage. In other embodiments described herein, the posterior segment pressure reference provided by the posterior segment pressure sensor (e.g., the sensor S1 shown in FIG. 2) may be used in lieu of an anterior segment pressure reference (e.g., for use in a passive GDD design). Allowing fluid (e.g., vitreous humor) to drain from the posterior segment allows for another mechanism of lowering or adjusting the IOP in addition to or instead of drainage from the anterior segment of the eye.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:
1. A method of implanting a treatment device into an eye of a patient, comprising:
inserting a drainage device including a flow system, an inlet tube, and an outlet tube into a subconjunctival space, wherein the inlet tube includes a proximal end coupled to the flow system in the subconjunctival space, and further wherein the inlet tube comprises internal spiral drainage features spaced along the length of an interior wall of the inlet tube to facilitate passage of fluid through the inlet tube portion;
passing a distal end of the inlet tube through a pars plana into a posterior segment of the eye; and
passing a distal end of the outlet tube into a drainage location of the eye.
2. The method of claim 1, wherein passing a distal end of the inlet tube through the pars plana into the posterior segment comprises passing the inlet tube through a sclera and a choroid of the eye before the distal end enters the posterior segment.

3. The method of claim 1, further including using a penetrating instrument to create a passageway for the distal end of the inlet tube from the subconjunctival space through the pars plana to the posterior segment.

4. The method of claim 3, wherein using a penetrating instrument to create a passageway for the distal end of the inlet tube from the subconjunctival space through the pars plana to the posterior segment comprises inserting the penetrating instrument through a sclera and a choroid of the eye into the posterior segment.

5. The method of claim 1, further including guiding the distal end of the inlet tube from the subconjunctival space through the pars plana to the posterior segment.

6. The method of claim 5, wherein guiding the distal end of the inlet tube from the subconjunctival space through the pars plana to the posterior segment comprises grasping the inlet tube with a guiding instrument.

7. The method of claim 1, wherein the distal end of the inlet tube includes sharp edges.

8. The method of claim 1, further including confirming the correct position of the inlet tube within the posterior segment by observing the location of a proximal marker on a proximal end of the inlet tube and a distal marker on the distal end of the inlet tube relative to anatomical landmarks of the eye.

9. The method of claim 1 wherein the drainage location is selected from the group of drainage locations consisting of: a subconjunctival space, a suprachoroidal space, a supraciliary space, a subscleral space, and episcleral vein, and a uveo-scleral outflow pathway.

10. The method of claim 1 wherein the internal spiral drainage features comprise rungs of a spiral shape extending between a proximal aperture of the inlet tube and a distal aperture of the inlet tube, the internal spiral drainage features arranged within the inlet tube to facilitate passage of fluid through the inlet tube from the proximal aperture to the distal aperture.

11. A treatment device for the drainage of fluid within an eye of a patient, comprising:
   a drainage tube having a lumen and comprising an inlet tube portion and an outlet tube portion, the drainage tube configured to convey fluid through the lumen from a posterior segment of the eye to a drainage location of the eye;
   a pressure sensor coupled to the inlet tube portion, the pressure sensor configured to measure posterior segment pressure; and
   a flow system in fluid communication with the drainage tube, the flow system configured to control intraocular pressure by throttling flow rates of the fluid through the drainage tube in response to changes in the posterior segment pressure measured by the pressure sensor,
   wherein the inlet tube portion is arranged to extend from the posterior segment to the flow system, and further wherein the inlet tube portion comprises internal spiral drainage features spaced along the length of an interior wall of the inlet tube portion to facilitate passage of fluid through the inlet tube portion.

12. The treatment device of claim 11, wherein the flow system is arranged to be positioned within the subconjunctival space.

13. The treatment device of claim 11, wherein the inlet tube portion includes a proximal end coupled to the flow system and a distal end arranged to be positioned within the posterior segment and an inlet tube lumen extending from the proximal end to the distal end.

14. The treatment device of claim 13, wherein the distal end includes sharp edges configured to pierce ocular tissue.

15. The treatment device of claim 13, wherein the inlet tube portion includes a plurality of apertures in communication with the lumen arranged so that fluid may enter the inlet tube portion through the plurality of apertures.

16. The treatment device of claim 13, wherein the outlet tube portion includes a plurality of apertures in communication with the lumen arranged so that fluid may exit the outlet tube portion through the plurality of apertures.

17. The treatment device of claim 11, wherein the flow system is actuatable in response to pressure differentials and is configured to control flow rates of the fluid along the drainage tube by shifting in response to pressure differentials between the posterior segment of the eye, the delivery site, and atmospheric pressure acting on the flow system or any combination thereof.

18. The treatment device of claim 17, wherein the flow system includes a pressure-driven valve system.

19. The treatment device of claim 18, wherein the flow system includes an electrically-driven pump system in fluid communication with the drainage tube and the pressure-driven valve system, the pump system being arranged to selectively control the flow of fluid through the drainage tube from posterior into the delivery site.

20. The treatment device of claim 19, wherein the pressure-driven valve system includes at least one flow control membrane.

21. The treatment device of claim 11, wherein the inlet tube portion includes a proximal marker on a proximal end of the inlet tube portion and a distal marker on the distal end of the inlet tube portion, the proximal and distal markers configured to indicate the position of the inlet tube portion within the eye.

22. The device of claim 11 wherein the drainage location is selected from the group of drainage locations consisting of: a subconjunctival space, a suprachoroidal space, a supraciliary space, a subscleral space, and episcleral vein, and a uveo-scleral outflow pathway.

23. The device of claim 11 wherein the internal spiral drainage features comprise rungs of a spiral shape extending between a proximal aperture of the inlet tube portion and a distal aperture of the inlet tube portion, the internal spiral drainage features arranged within the inlet tube portion to facilitate passage of fluid through the inlet tube portion from the proximal aperture to the distal aperture.

* * * * *